United States Patent
Levin (10) Patent No.: US 10,133,392 B1
(45) Date of Patent: Nov. 20, 2018

(54) SMARTPHONE NAIL POLISH

(71) Applicant: Larry Levin, Kansas City, MO (US)

(72) Inventor: Larry Levin, Kansas City, MO (US)

( * ) Notice: Subject to any disclaimer, the term of this patent is extended or adjusted under 35 U.S.C. 154(b) by 733 days.

(21) Appl. No.: 14/474,155

(22) Filed: Aug. 31, 2014

Related U.S. Application Data (60) Provisional application No. 61/856,117, filed on Jul. 19, 2013.

(51) Int. Cl.
| | |
|---|---|
| *G06F 3/041* | (2006.01) |
| *A61K 8/37* | (2006.01) |
| *A45D 34/04* | (2006.01) |
| *A61K 8/34* | (2006.01) |
| *A61K 8/73* | (2006.01) |
| *A61K 8/81* | (2006.01) |
| *A61K 8/19* | (2006.01) |
| *A61Q 3/02* | (2006.01) |

(52) U.S. Cl.
CPC ......... *G06F 3/0416* (2013.01); *A45D 34/045* (2013.01); *A61K 8/19* (2013.01); *A61K 8/34* (2013.01); *A61K 8/37* (2013.01); *A61K 8/731* (2013.01); *A61K 8/8152* (2013.01); *A61Q 3/02* (2013.01); *A61K 2800/40* (2013.01)

(58) Field of Classification Search
CPC ....... G06F 3/0416; A45D 34/045; A61K 8/19; A61K 8/34; A61K 8/37; A61K 8/731; A61K 8/8152; A61K 2800/40; A61Q 3/02
See application file for complete search history.

(56) References Cited

U.S. PATENT DOCUMENTS

| | | | | |
|---|---|---|---|---|
| 5,538,717 A | * | 7/1996 | La Poterie | A61K 8/70 424/401 |
| 5,965,111 A | * | 10/1999 | Ellingson | A61Q 3/02 424/401 |
| 6,200,045 B1 | * | 3/2001 | Hahn | A45D 34/06 401/126 |
| 6,207,322 B1 | * | 3/2001 | Kelsey | H01M 4/06 29/623.1 |
| 6,325,847 B1 | * | 12/2001 | Christie | C09C 1/0015 106/403 |
| 6,568,867 B1 | * | 5/2003 | Okamoto | A45D 34/045 401/126 |
| 6,626,598 B2 | | 9/2003 | Schneider | |

(Continued)

FOREIGN PATENT DOCUMENTS

| | | | | |
|---|---|---|---|---|
| WO | WO 0245663 A1 | * | 6/2002 | ............... A61K 8/44 |
| WO | WO 2011126575 A2 | * | 10/2011 | ............ A45D 31/00 |

(Continued)

OTHER PUBLICATIONS

APR: Breakthrough New Touch Technology From ELO Touch Systems—May 2006.

(Continued)

*Primary Examiner* — David Walczak
(74) *Attorney, Agent, or Firm* — Tumey L.L.P.

(57) ABSTRACT

A variety of methods and compositions for a new polish formulation that uses electro-conductive liquid to transfer static electricity between the human body and a touch screen. It will be primarily used by women to uses their nails while typing. The device will bring increased speed and accuracy while being worn.

14 Claims, 8 Drawing Sheets

(56) References Cited

U.S. PATENT DOCUMENTS

| | | | | |
|---|---|---|---|---|
| 8,157,463 | B2* | 4/2012 | McBratney | A46B 11/00 401/126 |
| 8,702,332 | B2* | 4/2014 | Hartstock | A45D 34/045 401/126 |
| 9,282,801 | B2* | 3/2016 | Yumoto | G06F 3/03545 |
| 9,713,585 | B2* | 7/2017 | Valia | A61K 8/585 |
| 9,753,551 | B2* | 9/2017 | Gottlieb | G06F 3/033 |
| 2002/0039513 | A1* | 4/2002 | Pink | A45D 34/045 401/129 |
| 2002/0099308 | A1* | 7/2002 | Bojan | A61B 5/14514 600/309 |
| 2003/0031496 | A1 | 2/2003 | Schneider | |
| 2009/0278818 | A1 | 11/2009 | Dinozzi et al. | |
| 2010/0039392 | A1* | 2/2010 | Pratt | G06F 3/039 345/173 |
| 2010/0297045 | A1* | 11/2010 | Kaupp | A61K 8/0229 424/59 |
| 2010/0303532 | A1* | 12/2010 | Brunozzi | A45D 34/00 401/6 |
| 2010/0329770 | A1* | 12/2010 | Volek | A45D 34/045 401/6 |
| 2011/0011416 | A1* | 1/2011 | Burns | A45D 31/00 132/73 |
| 2013/0076690 | A1 | 3/2013 | Vellanki | |
| 2014/0041677 | A1* | 2/2014 | Yumoto | G06F 3/03545 132/73 |
| 2015/0098971 | A1* | 4/2015 | Sacripante | A61K 8/85 424/401 |
| 2015/0252171 | A1* | 9/2015 | Molnar | C09D 105/00 106/31.69 |
| 2016/0295989 | A1* | 10/2016 | Hakeem | A45D 31/00 |
| 2016/0302550 | A1* | 10/2016 | Cody Teichner | A45D 31/00 |

FOREIGN PATENT DOCUMENTS

| | | |
|---|---|---|
| WO | 2014168475 | 10/2014 |
| WO | 2014168476 | 10/2014 |

OTHER PUBLICATIONS

Worlee—Cosmetic Raw Materials—Jan. 2011.
Sharp Kabushiki Kaisha, Artificial Nail and Nail Polish—WO2012137963-A1—Oct. 2012.
Stumpe—A New Principle for an X-Y Touch Screen—Mar. 1977.
Dow—Walsroder Nitrocellulose—Jun. 1998.
BYK—Additives & Instruments—Laponite—Oct. 2013.
Holl et al.—Experiments to Find a Manufacturing Process for an X-Y Touch Screen. Jan. 1978.
Beck and Stumpe—Two Devices for Operator Interaction in the General Control of the New Cern Accelerator—May 1973.
BYK—MSDS—Laponite—Oct. 2013.
Boyst, Silecky, and Thanedar—Smartphone Nail Polish—May 2014.

* cited by examiner

PRIOR ART

| Raw materials used in solvent-borne nail polish formulation ||
|---|---|
| Ingredient | Function |
| Ethyl Acetate | Solvent |
| Butyl Acetate | |
| Isopropanol | |
| Walsroder Nitrocellulose E400 | Film Former |
| Acrylate Copolymer | Film Support |
| Dioctyl terephtalate | Plasticizer |
| CHROMA-CHEM UCDTM V 1702 V | Conductive Agent |
| Carbon Black | |
| Silver coated glass flakes | |
| Raw materials used in water-borne nail polish formulation ||
| Worlée Micromer C70/61 | Film Former |
| Worlée Micromer C70/63 | |
| ME-S1885 Soy Methyl Ester | Plasticizer |
| Laponite XLS (10% in water) | Dispersing agent |
| StarLight (TM) FX 15 | Conductive Agent |
| Carbon Black | |
| Silver coated glass flakes | |
| Worlée Base AQ 77007/1 | Pigment |
| Worlée Base AQ 73360/1 | |

SMARTPHONE NAIL POLISH

CLAIM OF PRIORITY FROM RELATED APPLICATIONS

The present application claims priority from U.S. Provisional Patent Application No. 61/856,117 filed on Jul. 19, 2013 to Larry Levine Kansas City, (Mo.) directed to SMARTPHONE NAIL POLISH that is hereby incorporated by reference.

BACKGROUND OF THE INVENTION

Field of the Invention

The inventive device described in the instant application is a new polish formulation that uses electro-conductive liquid to transfer static electricity between the human body and touch screen. It will be primarily used by women to uses their nails while typing. The device will bring increased speed and accuracy in dialing a cellular phone while being worn.

Brief Description of the Prior Art

Conductive nail polishes are well known in the art. Various Patents and Published Patent applications are in fact directed to conductive nail polishes. While developing the invention of the instant application independently the Inventor researched extensively the public record as well as the current market for processes of producing half popped corn and the most relevant examples found in the search are mentioned in the Information Disclosure Statement (IDS) attached.

In the specific three references address the same problem resolved by the present invention: WIPO PCT 2012137963 A1 by Sharp Kaisha Kabushiki et al. (the Kabushiki reference), US published patent application 20110011416 by Burns, and US published patent application 20100039392 by Pratt et al. At the time of writing of the present application the Kabushiki reference is under examination in the national stage at the United States Patent and Trademark Office as U.S. Ser. No. 14/009,495.

The three application above try to address the general problem of providing some sort of conductive device that can be used to answer a phonecall on a cellular phone that has a touch screen while wearing extra long fingernails. A touchscreen is an electronic visual display that the user can control through simple or multi-touch gestures by touching the screen with a special stylus/pen and-or one or more fingers. Some touchscreens use an ordinary or specially coated gloves to work while others use a special stylus/pen only. The user can use the touchscreen to react to what is displayed and to control how it is displayed (for example by zooming the text size).

The touchscreen enables the user to interact directly with what is displayed, rather than using a mouse, touchpad, or any other intermediate device (other than a stylus, which is optional for most modern touchscreens).

Touchscreens are common in devices such as game consoles, personal computers, tablet computers, and smartphones. They can also be attached to computers or, as terminals, to networks. They also play a prominent role in the design of digital appliances such as personal digital assistants (PDAs), satellite navigation devices, mobile phones, and video games and some books (Electronic books).

The popularity of smartphones, tablets, and many types of information appliances is driving the demand and acceptance of common touchscreens for portable and functional electronics. Touchscreens are found in the medical field and in heavy industry, as well as for automated teller machines (ATMs), and kiosks such as museum displays or room automation, where keyboard and mouse systems do not allow a suitably intuitive, rapid, or accurate interaction by the user with the display's content.

Historically, the touchscreen sensor and its accompanying controller-based firmware have been made available by a wide array of after-market system integrators, and not by display, chip, or motherboard manufacturers. Display manufacturers and chip manufacturers worldwide have acknowledged the trend toward acceptance of touchscreens as a highly desirable user interface component and have begun to integrate touchscreens into the fundamental design of their products.

There are three basic systems that are used to recognize a person's touch:Resistive; Capacitive; and Surface acoustic wave. The resistive system consists of a normal glass panel that is covered with a conductive and a resistive metallic layer. These two layers are held apart by spacers, and a scratch-resistant layer is placed on top of the whole setup. An electrical current runs through the two layers while the monitor is operational. When a user touches the screen, the two layers make contact in that exact spot. The change in the electrical field is noted and the coordinates of the point of contact are calculated by the computer. Once the coordinates are known, a special driver translates the touch into something that the operating system can understand, much as a computer mouse driver translates a mouse's movements into a click or a drag.

In the capacitive system, a layer that stores electrical charge is placed on the glass panel of the monitor. When a user touches the monitor with his or her finger, some of the charge is transferred to the user, so the charge on the capacitive layer decreases. This decrease is measured in circuits located at each corner of the monitor. The computer calculates, from the relative differences in charge at each corner, exactly where the touch event took place and then relays that information to the touch-screen driver software. One advantage that the capacitive system has over the resistive system is that it transmits almost 90 percent of the light from the monitor, whereas the resistive system only transmits about 75 percent. This gives the capacitive system a much clearer picture than the resistive system.

On the monitor of a surface acoustic wave system, two transducers (one receiving and one sending) are placed along the x and y axes of the monitor's glass plate. Also placed on the glass are reflectors—they reflect an electrical signal sent from one transducer to the other. The receiving transducer is able to tell if the wave has been disturbed by a touch event at any instant, and can locate it accordingly. The wave setup has no metallic layers on the screen, allowing for 100-percent light throughput and perfect image clarity. This makes the surface acoustic wave system best for displaying detailed graphics (both other systems have significant degradation in clarity).

Another area in which the systems differ is in which stimuli will register as a touch event. A resistive system registers a touch as long as the two layers make contact, which means that it doesn't matter if you touch it with your finger or a rubber ball. A capacitive system, on the other hand, must have a conductive input, usually your finger, in order to register a touch. The surface acoustic wave system works much like the resistive system, allowing a touch with almost any object—except hard and small objects like a pen tip.

Now the problem is that both Resistive and Capacitive touch screen require some contact with an electrically charged surface. This contact is usually assured by the fingertips. On the other hand when a woman wears long fingernails, such as acrylic fingernails it becomes more difficult to effect to reach the screen with the fingertip because of the hindrance produced by the long fingernail. Fingernails and acrylic fingernails do not have the same electrical properties of human skin and reacts differently when they are placed in contact with the surface of a touch screen producing unconsistent results. It would be convenient to have a device that overcome such shortfall such as a set of fingernails that can efficiently transfer a sufficient amount of charge to the touch screen to produce a reliable effective touch.

Figure 1:
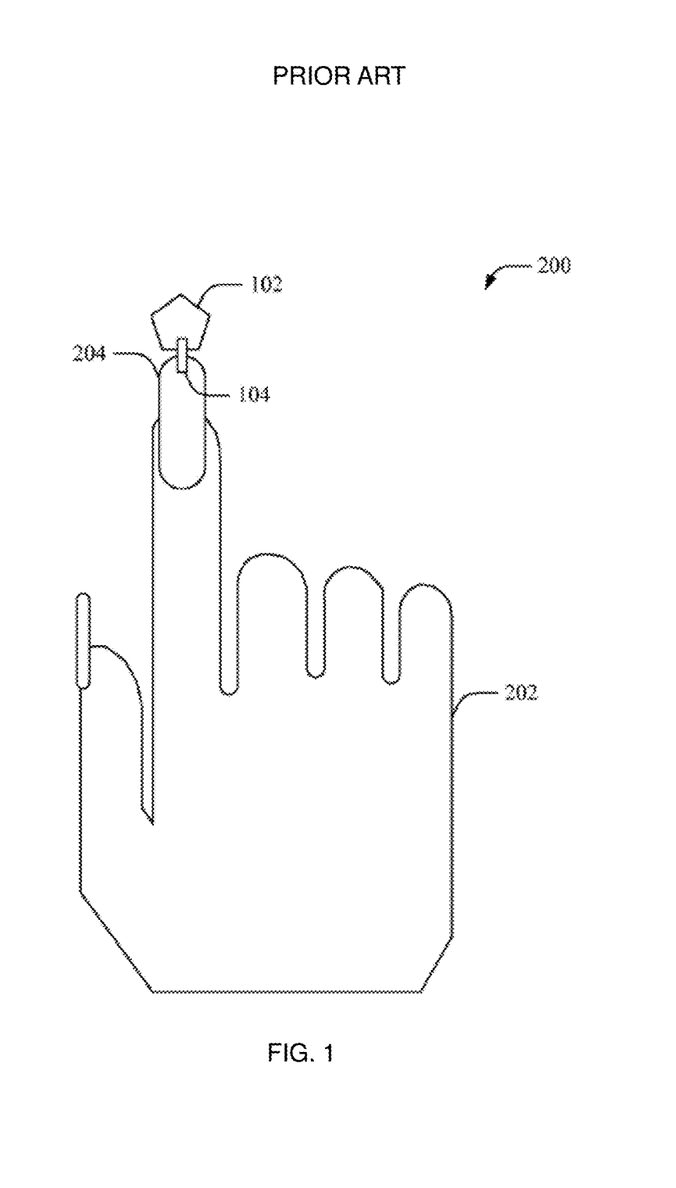
FIG. 1 the Pratt et al. device.

Now with specific reference to the Pratt et al. application, as shown in FIG. 1 it requires the inconvenient "pointing device" (102) and the bulky "attaching device" (104). The combination of pointing and attaching devices as thought in the Pratt et al. application lead to a final object that is inconvenient as not only is not aesthetic, but it is also not very practical. Additionally the attaching device 104 limits the surface of contact with the fingernail to a minimum raising therefore structural concerns.

Figure 2:
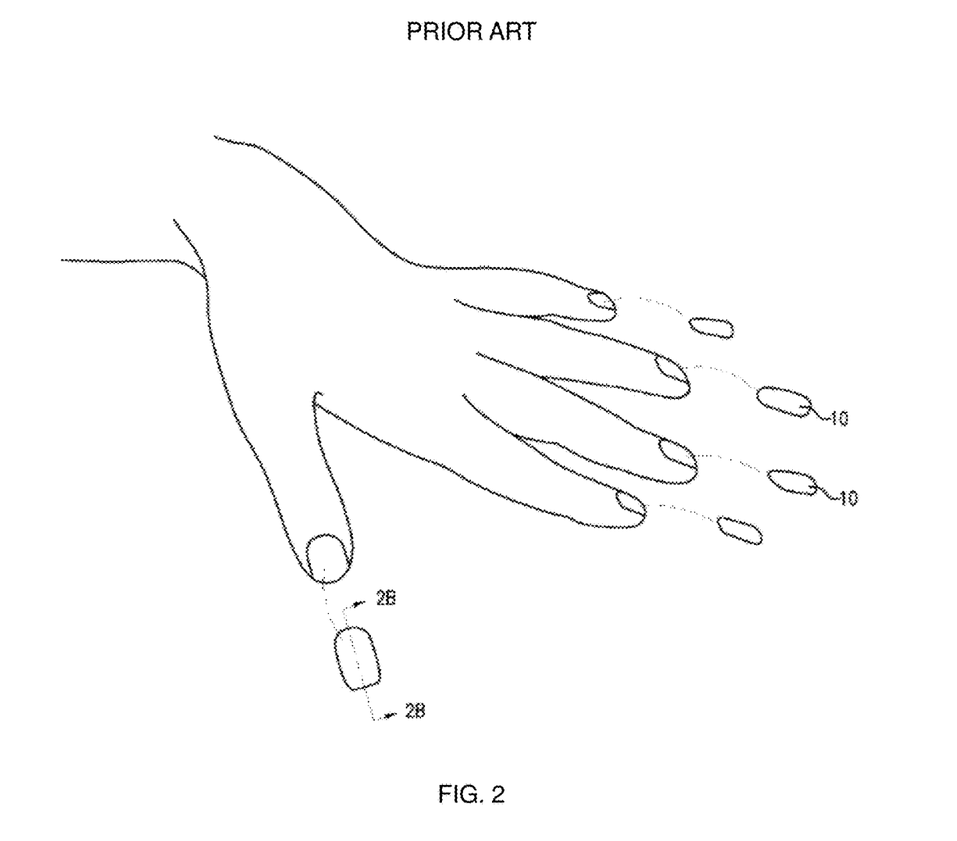
FIG. 2 the Burn device.

With specific reference to the Burns reference, as shown in FIG. 2 also that one suppose that one wears artificial nails (10) and (2b). While Burns provides a more practical solution to the problem of effectively punching a key on a touch screen it still involves the use of acrylic or artificial nail (10) and (2b) thus limiting its applicability to people that wear artificial nails.

There is the need in the art for a electrically active paint that can be applied directly to the nails regardless whether they are artificial or real to make sure that the user can make an efficient electrical contact with the touch screen. This seems to be provided by the Kabushiki reference. On the other hand the Kabuishiki reference is not enabling because it teaches and suggests a number the use of a nail polish using conducting material. But then all the practical statement are not defined under 35 USC 112. For example the Kabushiki reference define the amount of conducting material as "having the appropriate level of electrical conductivity so that a touch operation on a capacitive touch panel is possible" but it does not positively break down which is the conductivity material, neither hints the amount of conductivity material needed to achieve the aimed results.

35 USC 112 (a) literally recites: The specification shall contain a written description of the invention, and of the manner and process of making and using it, in such full, clear, concise, and exact terms as to enable any person skilled in the art to which it pertains, or with which it is most nearly connected, to make and use the same, and shall set forth the best mode contemplated by the inventor or joint inventor of carrying out the invention.

Figure 3:
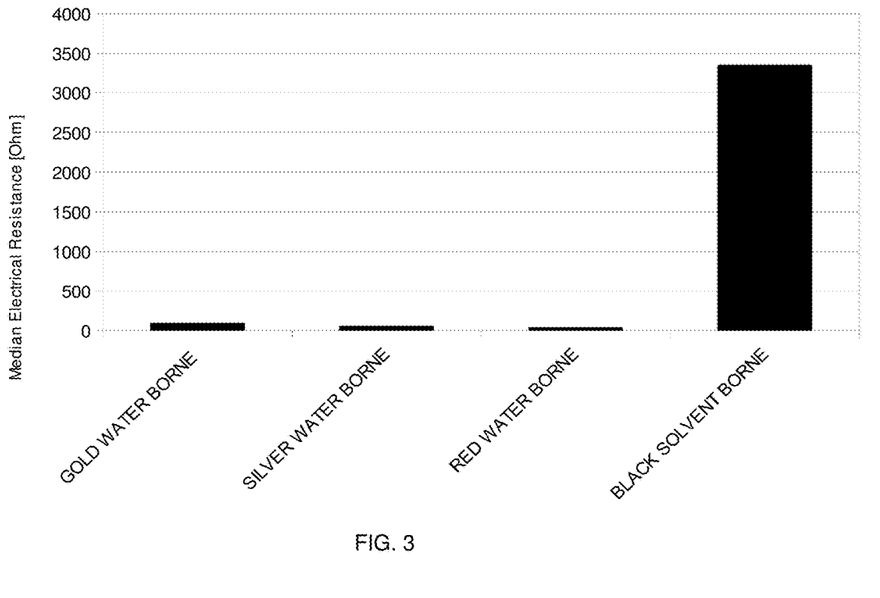
FIG. 3 Graph of electrical conductivity of four different conductive nailpolishes respectively Gold waterborn, Silver waterborn, Red waterborn, and Black solvent born. The graph shows that a conductivity nailpolish realized by mixing ethyl acetate, butyl acetate, and isopropanol, slowly adding nitrocellulose and black carbon particles, and finally adding the dioctyl terephthalate features an electrical resistance much higher than the other three conductive nailpolishes.
Figure 4:
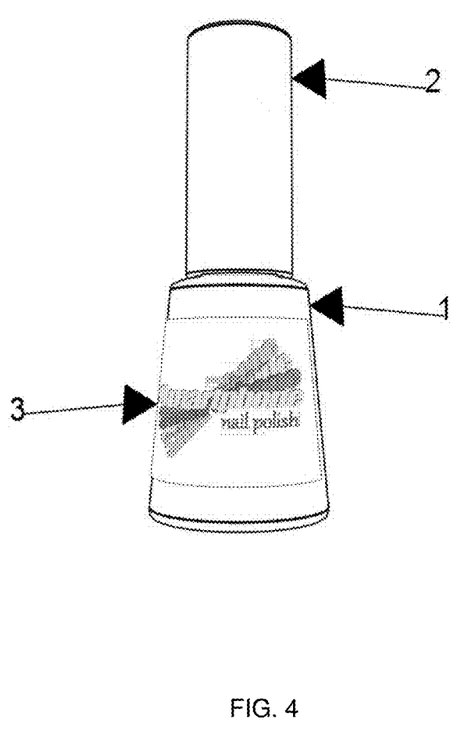
FIG. 4 is a frontal elevation view of one of the preferred embodiments of "Smartphone Nail Polish" in accordance with the teachings of the present invention.
Figure 5:
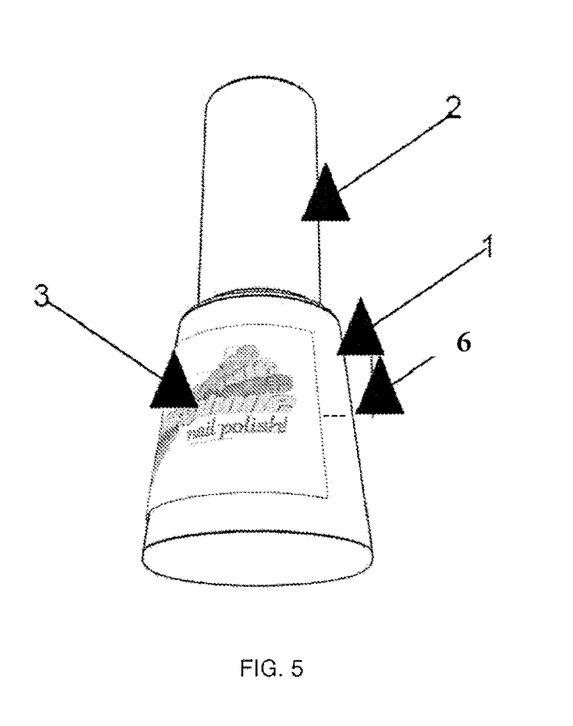
FIG. 5 is a bottom perspective view of "Smartphone Nail Polish" of FIG. 1.
Figure 6:
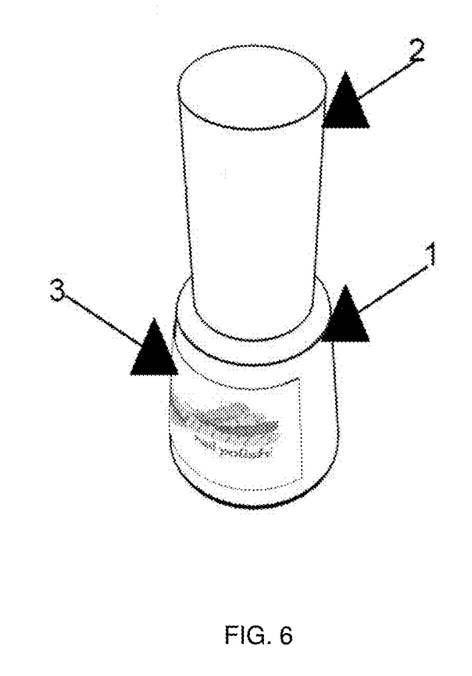
FIG. 6 is a top perspective view of "Smartphone Nail Polish" of FIG. 1.
Figure 7:
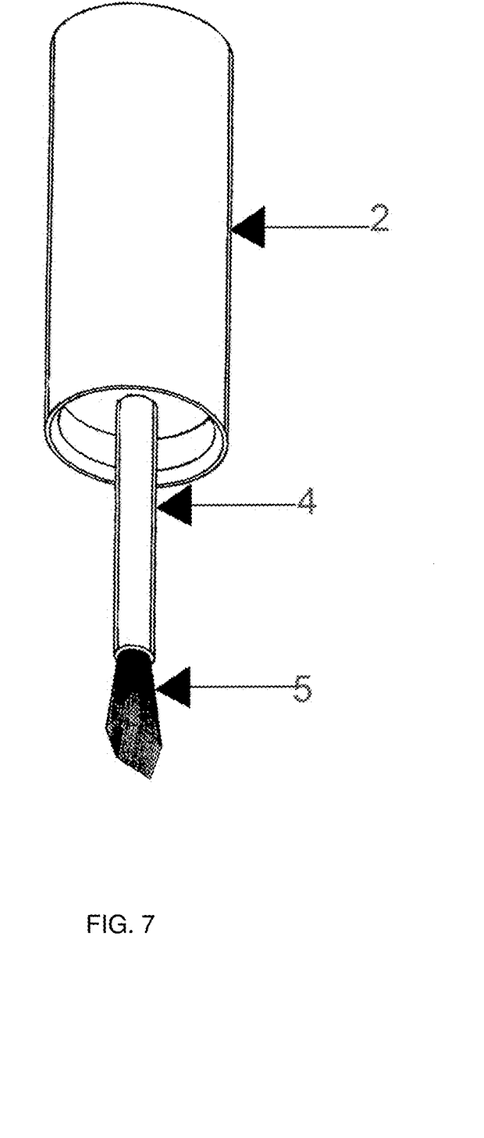
FIG. 7 is a bottom perspective view of "Smartphone Nail Polish"'s cap of FIG. 1.
Figure 8:
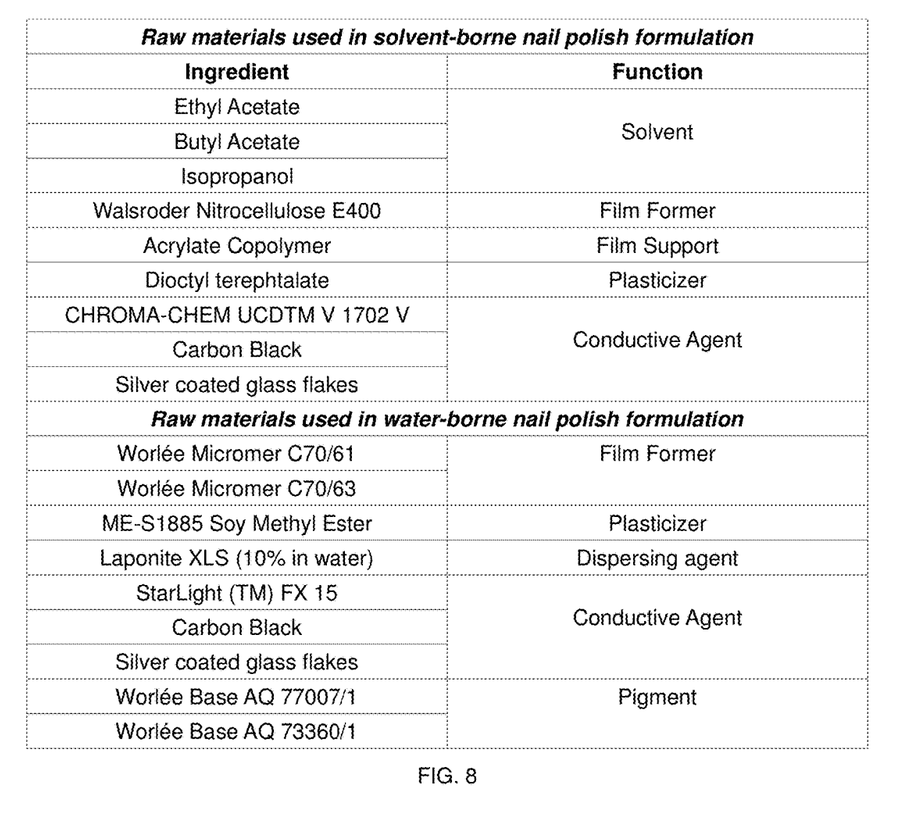
FIG. 8 is a table illustrating the different components used respectively for the base formulation of the solvent borne conductive nail polish and for the water borne conductive nail polish.

In FIG. 3 the electrical resistance in Ohm ($\Omega$) of different combinations of conductive material with substrates is graphed showing huge differences depending on the kind of combination selected. The information given by the Kabuishiki reference are not sufficient to practice the invention without undue experimentation. Therefore despite all the efforts listed above prior art patents describe structures that are either not truly convenient or else involve complicated, expensive, and overly difficult assembly and/or disassembly parts and procedures. Other devices have been advertised on various media but never patented or described into a printed publication.

SUMMARY OF THE INVENTION

The inventive device described in the instant application is a new polish formulation that uses electro-conductive liquid to transfer static electricity between the human body and touch screen. It will be primarily used by women to uses their nails while typing. The device will bring increased speed and accuracy while being worn. The mechanism of the invention is a removable cap with brush attached that can brush the electro-conductive nail polish from the reservoir onto the top and bottom edge of a nail.

It is then the principal object of the present invention is to provide women with long or medium length nails the ability to use a touch screen with increased accuracy and speed.

It is a secondary objective of the present invention to eliminate the problems of hitting several keys at the same time on the touch screen. It is an additional objective of the present invention to provide a device that does not rust or deteriorate over time. It is a final objective of the present invention to provide for a device that is relatively inexpensive to build, but that can eventually be sold at a premium.

These and other objective achieved by the device of the present invention will be apparent by the drawings, by their detailed description, and by the specification here from appended.

DESCRIPTION OF THE PREFERRED EMBODIMENT

The inventive device described in the instant application is a new polish formulation that uses electro-conductive liquid to transfer static electricity between the human body and touch screen. It will be primarily used by women to uses their nails while typing. The device will bring increased speed and accuracy while being worn. The mechanism of the invention is a removable cap with brush attached that can brush the electro-conductive nail polish from the reservoir onto the top and bottom edge of a nail.

The Smartphone Nail Polish are designed to be a nail polish with the ability to transfer static electricity from a human to a touch screen. This device can be used by women with medium to long nail as well as regular sized nail for the electro-conductive liquid allows for the use of a touch screen. In one preferred embodiment of "Smartphone Nail Polish" of the present application will be a nail polish with a different color and finish.

The invention is an electro-conductive liquid used in a nail polish formula that will make it possible for women to use just the tips of the nails when using their touch screens on various mobile devices. This nail polish can be applied to the underside of the nails as well as the top for best results. With this kind of application, there will be a concentration of the liquid around the tip of the nails. The premise is to provide a simple way for women with longer nails to use a touch screen efficiently. This is not limited to being used only on their own smartphones it can also be used on tablets, ATMs, or cashiers touch screens.

Users will have a convenient way of accurately using a touch screen without the need of cutting their nails. The "Smart Phone Nail Polish" provides a quick for female users to accurately use a touch screen.

Electro-conductive fiber of carbon painting will also be incorporated in this nail polish. It will be available in a variety of fashionable colors to suit individual tastes. This same electro-conductive liquid can be incorporated and molded into the artificial glue-on nails so similar benefits can be achieved by those who wear these nails. It can also be used with the Gel Nails processes which are popular today.

Nail polish is a lacquer that can be applied to the human fingers or toe nails to decorate and protect the nail plate. The formulation has been revised repeatedly to enhance its decorative effects and to suppress cracking or flaking. Nail polish consists of an organic polymer with various additives.

A touchscreen is an electronic visual display that the user can control through simple or multi-touch gestures by touching the screen with a special stylus/pen and-or one or more fingers. Some touchscreens use an ordinary or specially coated gloves to work while others use a special stylus/pen only. The user can use the touchscreen to react to what is displayed and to control how it is displayed.

Specifically speaking capacitive touchscreen panel consists of an insulator such as glass, coated with a transparent conductor such as indium tin oxide (ITO). As the human body is also an electrical conductor, touching the surface of the screen results in a distortion of the screen's electrostatic field, measurable as a change in capacitance. Different technologies may be used to determine the location of the touch.

The location is then sent to the controller for processing. Unlike a resistive touchscreen, one cannot use a capacitive touchscreen through most types of electrically insulating material, such as gloves. This disadvantage especially affects usability in consumer electronics, such as touch tablet PCs and capacitive smartphones in cold weather. It can be overcome with a special capacitive stylus, or a special-application glove with an embroidered patch of conductive thread passing through it and contacting the user's fingertip.

The largest capacitive display manufacturers continue to develop thinner and more accurate touchscreens, with touchscreens for mobile devices now being produced with 'in-cell' technology that eliminates a layer, such as Samsung's Super AMOLED screens, by building the capacitors inside the display itself. This type of touchscreen reduces the visible distance (within millimeters) between the user's finger and what the user is touching on the screen, creating a more direct contact with the content displayed and enabling taps and gestures to be more responsive.

A simple parallel plate capacitor has two conductors separated by a dielectric layer. Most of the energy in this system is concentrated directly between the plates. Some of the energy spills over into the area outside the plates, and the electric field lines associated with this effect are called fringing fields. Part of the challenge of making a practical capacitive sensor is to design a set of printed circuit traces which direct fringing fields into an active sensing area accessible to a user. A parallel plate capacitor is not a good choice for such a sensor pattern. Placing a finger near fringing electric fields adds conductive surface area to the capacitive system. The additional charge storage capacity added by the finger is known as finger capacitance, CF. The capacitance of the sensor without a finger present is denoted as CP in this article, which stands for parasitic capacitance.

In one of its preferred embodiments the inventive device of the present application embodies an electro-conductive liquid nail polish comprises: A 40 fl. Oz. glass container (1) which is closed with a plastic cap (2) with the brand name and color sticker (3) on the outside. The plastic cap (2) has an adjoined wand (4) to dip the application brush (5) into the electro-conductive nail polish (6).

Still in a separate preferred embodiment of the electrically active nailpolish of the present application said electrically active nailpolish is composed by a mix of solvents; a film former; a pigment; and a conducting agent. Said mix of solvents may include: Ethyl Acetate, Butyl Acetate, and Isopropanol in relative percentages of 38.6%, 35.6%, and 26.6. Said film former may be Nitrocellulose and in that case it requires the use of an acrylate copolymer. In a further special embodiment of the electrically active nailpolish of the present application where nitrocellulose is used said nitrocellulose is commercially available Walsorder Nitrocellulose E400.

A plasicizer such as Dioctyl terephtalate, or Soy methyl Esther may be further added to the composition above while said conductive agent is selected from the group consisting of silver coated glass flakes, gold coated glass flakes, and black carbon. A dispersing agent may be added to the base composition and said dispersing agent may be Laponite, preferably dissolved in a 10% water mixture.

A method of making an electrically active nailpolish is also claimed that comprises the steps of: Combining the ethyl acetate, butyl acetate, and isopropanol in a large beaker; slowly add the nitrocellulose while; using a low sheer mixer, and once all the nitrocellulose has been added, covering the top of the beaker; continuing stirring the mixture until all of the nitrocellulose has dissolved into solution; slowly adding the acrylic copolymer to the solution; continuing stirring the mixture until all of the acrylic copolymer has dissolved into solution; adding the dioctyl terephthalate to the solution; allowing the mixture to mix for approximately five minutes.

According to the method above the relative mass proportion of the ingredients are: Ethyl Acetate 28.5%; Butyl Acetate 26.3%; Isopropanol 18.9%; Nitrocellulose 10.5%; Acrylic copolymer 7.4%; and Dioctyl Terephthalate 8.4%.

In the development of the electrically active nailpolish of the present application an extensive study was conducted by AVOMEN ANALYTICAL SERVICES whose results are summarized in a report quoted in the IDS and incorporated by reference in the present application. During this study three kinds of electrically active nailpolishes were developed: a solvent born conductive nailpolish; a black solvent born conductive nailpolish, and a water born conductive nailpolish.

The steps the production of the solvent born conductive nail_polish_include: Combine the ethyl acetate, butyl acetate, and isopropanol in a large beaker; Using a low sheer mixer, slowly add the nitrocellulose. Once all the nitrocellulose has been added, cover the top of the beaker. Continue stirring the mixture until all of the nitrocellulose has dissolved into solution; Slowly add the acrylic copolymer to the solution. Continue stirring the mixture until all of the acrylic copolymer has dissolved into solution. Add the dioctyl terephthalate to the solution. Allow the mixture to mix for five minutes.

The steps for the production of the black solvent born conductive nailpolish include: Place the solvent-borne nail polish base in a separate container and under medium sheer add the CHROMA-CHEM® UCDTM V 1702V; then add the remaining butyl acetate and cover the container. Allow the solution to mix until the CHROMA-CHEM® UCDTM V 1702V is well dispersed in the solution.

The steps for the production of the water born conductive nailpolish include: Under a medium sheer of a mixer, add the WorléeMicromer C70/61 and WorléeMicromer C70/63 to the container, and mix the solution of the WorléeMicromer C70/61 and WorléeMicromer C70/63 well. Slowly add the ME-S1885 Soy Methyl Ester and the Laponite XLS (10% in water) to the container. Mix the solution until a homogenous solution is obtained.

With regards to the color the steps for the production of a Gold water born conductive nailpolish include: Add the StarLight™ FX 15 to the water-borne nail polish base under medium sheer. Sonicate the mixture to evenly disperse the StarLight™ FX 15. StarLight™ FX 15 is a Trademarked product consisting of silver covered glass flakes. The Worlee base are base row materials for the production of cosmetics whose composition is broken down in the Worlee technical manuals attached in the IDS that are hereby incorporated by reference.

With regards to the color the steps for the production of a Red water born conductive nailpolish include: Add the StarLight™ FX 15 and the WorléeBase AQ 77007/1 to the water-borne nail polish base under medium sheer. Sonicate the mixture to evenly disperse the StarLight™ FX 15 and WorléeBase AQ 73360/1. Finally the steps for the production of a Silver water born conductive nailpolish include: Add the StarLight™ FX 15 and the WorléeBase AQ 77007/1 to the water-borne nail polish base under medium sheer. Sonicate the mixture to evenly disperse the StarLight™ FX 15 and WorléeBase AQ 77007/1.

Sonication is the act of applying sound energy to agitate particles in a sample, for various purposes. Ultrasonic frequencies (>20 kHz) are usually used, leading to the process also being known as ultrasonication or ultra-sonication. In the laboratory, it is usually applied using an ultrasonic bath or an ultrasonic probe, colloquially known as a sonicator. In a paper machine, an ultrasonic foil can distribute cellulose fibres more uniformly and strengthen the paper.

Sonication has numerous effects, both chemical and physical. The chemical effects of ultrasound are concerned with understanding the effect of sonic waves on chemical systems, this is called sonochemistry. The chemical effects of ultrasound do not come from a direct interaction with molecular species. Studies have shown that no direct coupling of the acoustic field with chemical species on a molecular level can account for sonochemistry or sonoluminescence. Instead, sonochemistry arises from acoustic cavitation: the formation, growth, and implosive collapse of bubbles in a liquid.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An electro-conductive nail polish device comprising:
a container that is that is labeled with a
sticker on the outside and is closed with a
plastic cap that has a
wand to dip
a brush into
a nail polish,
wherein the nail polish comprises:
   a solvent-borne nail polish base, wherein the solvent-borne nail polish base comprises: a mix of solvents, nitrocellulose, acrylic copolymer, and dioctyl terephthalate, wherein the mix of solvents comprises ethyl acetate, butyl acetate, and isoproponal, wherein the relative proportion of said ethyl acetate, butyl acetate, and isopropanol are respectively: 38.6%, 35.6%, and 26.6%; and
   a conducting agent, wherein the conducting agent comprises black carbon.

2. The electro-conductive nail polish of claim 1 where said container is made of glass.

3. The electro-conductive nail polish of claim 2 where said glass or plastic container can hold 0.40 fl. Oz. of a liquid.

4. An electrically active nail polish composed by
a mix of solvents, wherein the mix of solvents include ethyl acetate, butyl acetate, and isoproponal, wherein the relative proportion of said ethyl acetate, butyl acetate, and isopropanol are respectively: 38.6%, 35.6%, and 26.6%;
a film former;
a pigment; and
a conducting agent.

5. The electrically active nail polish of claim 4 where said film former is Nitrocellulose.

6. The electrically active nail polish of claim 4 further comprising an acrylate copolymer.

7. The electrically active nail polish of claim 4 where said conductive agent are silver coated glass flakes.

8. The electrically active nail polish of claim 4 where said conductive agent are gold coated glass flakes.

9. The electrically active nail polish of claim 4 where said conductive agent is black carbon.

10. The electrically active nail polish of claim 4 further comprising a dispersing agent.

11. The electrically active nail polish of claim 10 where said dispersing agent is a 10% solution of Laponite in water.

12. An electrically active nail polish composition comprising:
   a solvent-borne nail polish base wherein the solvent-borne nail polish base comprises: a mix of solvents, nitrocellulose, acrylic copolymer, and dioctyl terephthalate, wherein the mix of solvents comprises ethyl acetate, butyl acetate, and isoproponal, wherein the relative proportion of said ethyl acetate, butyl acetate, isopropanol, nitrocellulose, acrylic copolymer, and dioctyl terephthalate are respectively: 28.5%, 26.3%, 18.9%, 10.5%, 7.4%, and 8.4%; and
   a conducting agent, wherein the conducting agent is black carbon.

13. The electrically active nail polish composition of claim 12, wherein the electrically active nail polish composition further comprises additional butyl acetate.

14. The electrically active nail polish composition of claim 13, wherein solvent-born nail polish base further comprising a dispersing agent comprising a solution of Laponite in water.

* * * * *